(12) United States Patent
Kauffman et al.

(10) Patent No.: US 11,925,358 B2
(45) Date of Patent: Mar. 12, 2024

(54) SURGICAL CUTTING APPARATUS

(71) Applicant: Worcester Polytechnic Institute, Worcester, MA (US)

(72) Inventors: Jesse Kauffman, Bryn Mawr, PA (US); Karim A. Tarabein, Cleveland, OH (US); Cameron W. Downey, Boston, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 176 days.

(21) Appl. No.: 17/244,825

(22) Filed: Apr. 29, 2021

(65) Prior Publication Data

US 2021/0338252 A1 Nov. 4, 2021

Related U.S. Application Data

(60) Provisional application No. 63/018,099, filed on Apr. 30, 2020.

(51) Int. Cl.
*A61B 17/16* (2006.01)
*A61B 17/3213* (2006.01)
*A61B 17/00* (2006.01)

(52) U.S. Cl.
CPC ...... *A61B 17/1604* (2013.01); *A61B 17/3213* (2013.01); *A61B 2017/0046* (2013.01); *A61B 2017/00477* (2013.01)

(58) Field of Classification Search
CPC .................. A61B 17/1604; A61B 17/3213
See application file for complete search history.

(56) References Cited

U.S. PATENT DOCUMENTS

| 5,649,946 A | 7/1997 | Bramlet |
| 5,653,712 A | 8/1997 | Stern |
| 5,653,713 A * | 8/1997 | Michelson ......... A61B 17/1611 606/184 |
| 9,642,621 B2 | 5/2017 | Belson et al. |

(Continued)

FOREIGN PATENT DOCUMENTS

JP 2014226214 A 12/2014

OTHER PUBLICATIONS

International Search Report, PCT/US2021/029996, dated Aug. 12, 2021, pp. 1-2.

*Primary Examiner* — Sameh R Boles
(74) *Attorney, Agent, or Firm* — Armis IP Law, LLC (57) ABSTRACT

A surgical rongeur device has an interchangeable, locking tip at a cutting end for engageable replacement with a variety of cutting tips for facilitating sterilization and blade changes. A detachable linkage between a handle portion and an interchangeable cutting tip (tip) provides a strong connection for actuation by the handle end but allowing for tip replacement via slidable, lateral displacement of the tip. The tip includes a blade and footplate formed from an amorphous metal for longevity and strength advantages. A handle provides a lever to actuate the tip from slidable communication via the detachable linkage. An interlocking member extends longitudinally from the handle into an internal slot on the tip for locking the tip by preventing lateral movement out of alignment with the handle. The aligned tip is responsive to actuation from the handle via a rail for disposing the blade longitudinally against the footplate.

12 Claims, 13 Drawing Sheets

(56) References Cited

U.S. PATENT DOCUMENTS

2004/0181250 A1* 9/2004 Adams ............. A61B 17/32002
                                                            606/170
2016/0302801 A1   10/2016 Redmond et al.
2020/0107961 A1    4/2020 Kahook et al.

* cited by examiner

SURGICAL CUTTING APPARATUS

RELATED APPLICATIONS

This patent application claims the benefit under 35 U.S.C. § 119(e) of U.S. Provisional Patent App. No. 63/018,099, filed Apr. 30, 2020, entitled "SANITARY KERRISON RONGEUR," incorporated herein by reference in entirety.

BACKGROUND

A rongeur is a surgical device for extracting tissue and bone by actuation of a blade against a footplate which secures the excised material for extraction from the surgical field to avoid deposition of remnants of excised material in the surgical region. A rigid metal construction provides necessary strength for cutting ability, but mandates cleaning and sterilization between uses. A number of rongeur devices of various sizes are often employed in a surgical procedure, each requiring subsequent cleaning and sterilization before reuse. A particularly popular surgical rongeur is the Kerrison rongeur, named for its creator, English physician Robert Masters Kerrison (1776-1847).

The general operation includes a lever actuated blade forced against a footplate for severing tissue as the blade compresses against the footplate. The blade may have a "U" or square shape that defines an excision region, and the footplate and blade extend in an opposed manner to form a jaw that closes upon actuation. Small but precise cuts of bone, cartilage, or other hard or soft tissue may be excised by a series of actuations which retain the excised tissue in a cavity defined by the blade until removed from the surgical site.

SUMMARY

A surgical cutting apparatus has an interchangeable, locking tip at a cutting end for engageable replacement with a variety of cutting tips for facilitating sterilization and blade changes. A detachable linkage between a handle portion and an interchangeable cutting tip (tip) provides a strong connection for actuation by the handle end but allowing for tip replacement via slidable, lateral displacement of the tip. The tip includes a blade and footplate formed from an amorphous metal for longevity and strength advantages. A handle provides a lever to actuate the tip from slidable communication via the detachable linkage. An interlocking member extends longitudinally from the handle into an internal slot on the tip for locking the tip by preventing lateral movement out of alignment with the handle. The aligned tip is responsive to actuation from the handle via a rail for disposing the blade longitudinally against the footplate.

In the configurations herein, the surgical cutting apparatus takes the form of a Kerrison Rongeur, although other styles of rongeur devices may benefit from the approach herein. Normally, several of these devices are needed for a single surgery, which means several of these will need to be sterilized extensively. With a swappable/disposable tip, we obviate the need to bring in several reusable devices that require expensive re-sterilization, and instead they can bring in a single device and dozens of disposable shafts to swap out. Surgeons have pointed out their main issue is maintaining sharpness, while there is evidence that hospitals have more issue with the additional costs of cleaning these instruments.

Configurations herein are based, in part, on the observation that Kerrison Rongeurs are precision medical instruments often formed from specialized fabrication techniques including stainless steel and other durable materials. Unfortunately, conventional approaches suffer from the shortcoming that blade sharpness and sterility are all significant factors that limit the number of times a Kerrison Rongeur may be used before sharpening, sterilizing, or outright discarding. This increases the expense of use, and may incentivize extended usage of blades before discarding or sharpening. The result is a functional but less precise blade edge that may compromise optimal results.

Accordingly, configurations herein substantially overcome the shortcomings of high cost and maintenance (sharpening) cycles by providing a disposable tip attaching via a detachable linkage to the handle of the rongeur that allows transfer of the actuation force for usage, but detaches easily for replacement with a sharper or sterilized blade while the handle is reusable. The tip and blade assembly may be formed in whole or in part using an amorphous metal that retains sharpness and has favorable strength and weight characteristics. A hybrid design may combine overmolded members for facilitating strength, cost and/or fabrication advantages. In this manner, a replacement for sharpness, sterility or blade shape need only replace the interchangeable tip rather than the entire device, and the replaced tip may be separately sharpened or sterilized for additional usage cycles.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

The description below presents an example of the surgical cutting apparatus having an interchangeable tip depicted as a Kerrison Rongeur device. The surgical cutting apparatus has a removable and/or disposable tip to facilitate surgical use of different sizes rongeur tips and blades on the same handle and device body. The surgical device includes an elongated body formed from a metal glass and having a slidable insert for controlling a blade, and a handle extending at an angle to the elongated body and having a hinged attachment to an actuator. A linkage between the actuator and the slidable insert disposes the slidable insert axially responsive to hinged movement of the actuator when depressed or "squeezed" by a surgeon/operator. A removable tip has a detachable linkage to a tip defining the distal end of the elongated body, while the handle extends from a proximate end of the elongated body. A blade is disposed in the removable tip, and is adapted for advancement against the cutting footplate by the slidable insert via the detachable engagement.

A homogenously formed leaf spring extends between the handle and the actuator, such that the leaf spring is responsive to compression for aligning the actuator in or near a parallel arrangement with the handle through hinged movement, and for biasing the actuator at an angle from the handle based on decompression/extension of the leaf spring. Homogenous construction with the handle and the body imparts the surface properties of the metal glass for minimizing post-processing needed for use.

The detachable engagement of the removable tip includes opposed, tapered protrusions, such that the tapered protrusions each define a respective cleat adapted to engage a receptacle. The disposable tip and elongated body have corresponding cleat/receptacle profiles that allow lateral engagement as the disposable tip slides into engagement from the side to allow forward, longitudinal sliding movement of the actuator, slidable insert and blade as a single unit.

Components of the disposable tip are designed to be injection molded out of the metal glass for homogenous construction, or may combine separately molded parts. For example, a polymer overmold may be provided on the disposable tip for supplementing metal glass blade and footplate components. Blade actuation is bi-directional such that squeezing the handle as shown in the figures below closes the Kerrison "jaw" (moves blade towards footplate), and releasing the handle opens the Kerrison "jaw" which subsequently releases the cut material (blade retracts away from footplate).

Figure 1A:
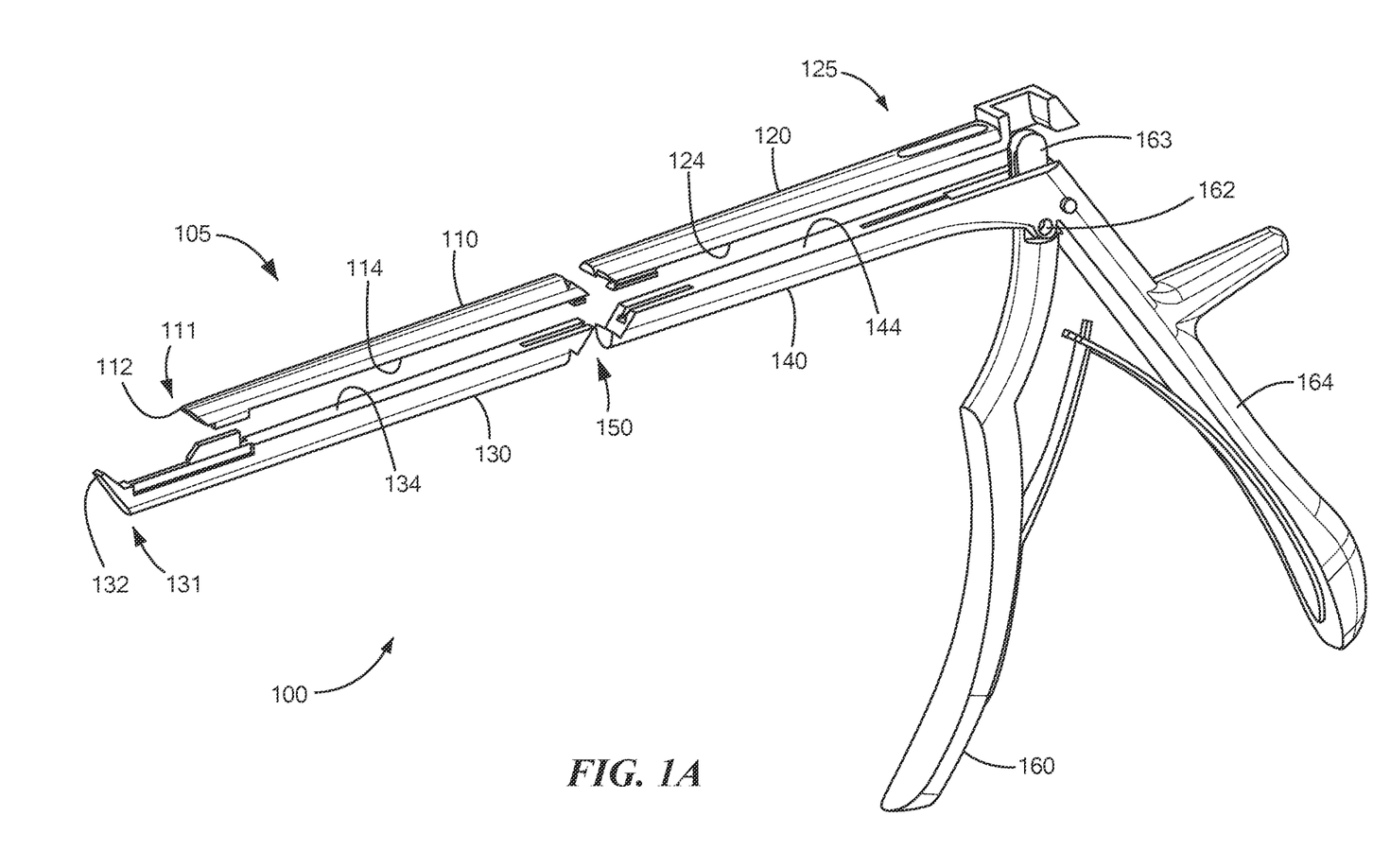
FIGS. 1A and 1B are perspective views of the interchangeable rongeur device according to configurations herein.
Figure 1B:
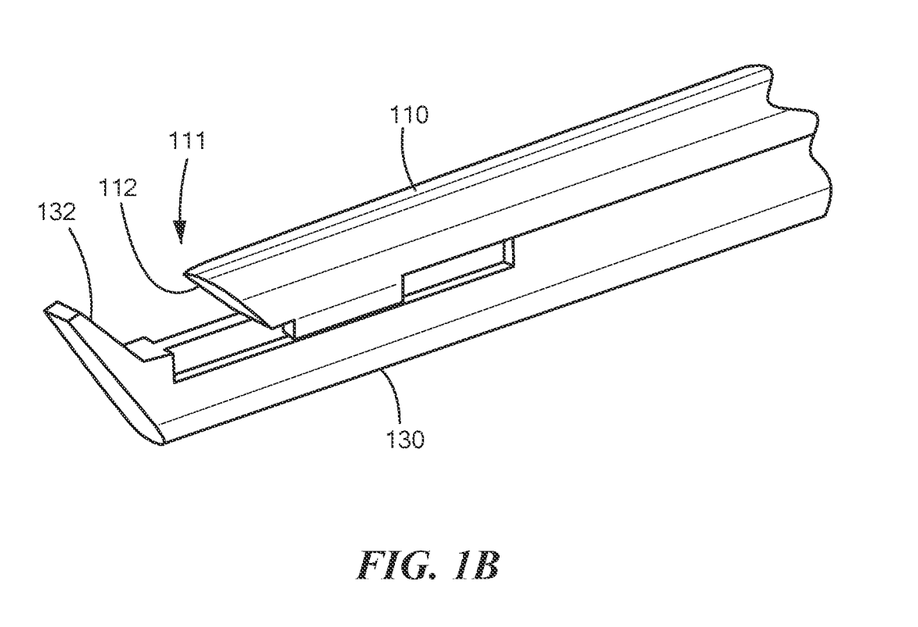

FIGS. 1A and 1B are perspective views of the interchangeable rongeur device according to configurations herein. In a particular arrangement, a medical cutting device 100 having interchanging blades includes a blade 112 disposed adjacent to a footplate 132 for engaging with the footplate to sever surgical material. A lever 160 pivots about a pivot axis 162 on a handle 125 for disposing the blade 112 against the footplate 132. An interchangeable tip 105 includes the blade 112, footplate 132 and a rail 134, arranged such that the blade 112 is in slidable communication with the rail 134 for actuation against the footplate 132. The handle 125 further includes a handle slide 120 and a handle base 140. A detachable linkage 150 between the handle 125 and the tip 105 is operable for disengaging the tip, discussed in further detail below.

The tip 105 includes a blade portion 110 and a footplate portion 130, in which the blade 112 attaches to a distal end 111 of the blade portion 110 and the footplate 132 attaches to a distal end 131 of the footplate portion 130 and is aligned for communication with the blade 112 by sliding along rail 134. A rail 144 on the handle is aligned longitudinally with the rail 134 on the tip when engaged by the detachable linkage 150, such that the blade portion 110 is responsive to the lever 160 via the handle slide 120 and the aligned rail 134, 144 to dispose the blade 112 against the footplate 132 for cutting and excising surgical material (bone, cartilage, etc.), as depicted in FIG. 1B. The rail 134 on the tip is attached to the footplate portion 130 and aligned with the rail 144 on the handle base 140, and the handle slide and blade portion are linked and sequentially engaged by the detachable linkage for slidable communication along the rail 134/144. The rail may be a variance in the contours that allow a slidable interlock, or may be defined by a flat surface for reduced friction. Each rail 134, 144 has a complementary slot or receiver 114, 124, respectively. In operation, lever 160 actuation by pulling towards a grip 164 causes the lever 160 to pivot around the pivot axis 162, which forces a protrusion 163 to force the handle slide 120 forward for engaging the blade, 112, discussed further below.

Figure 2A:
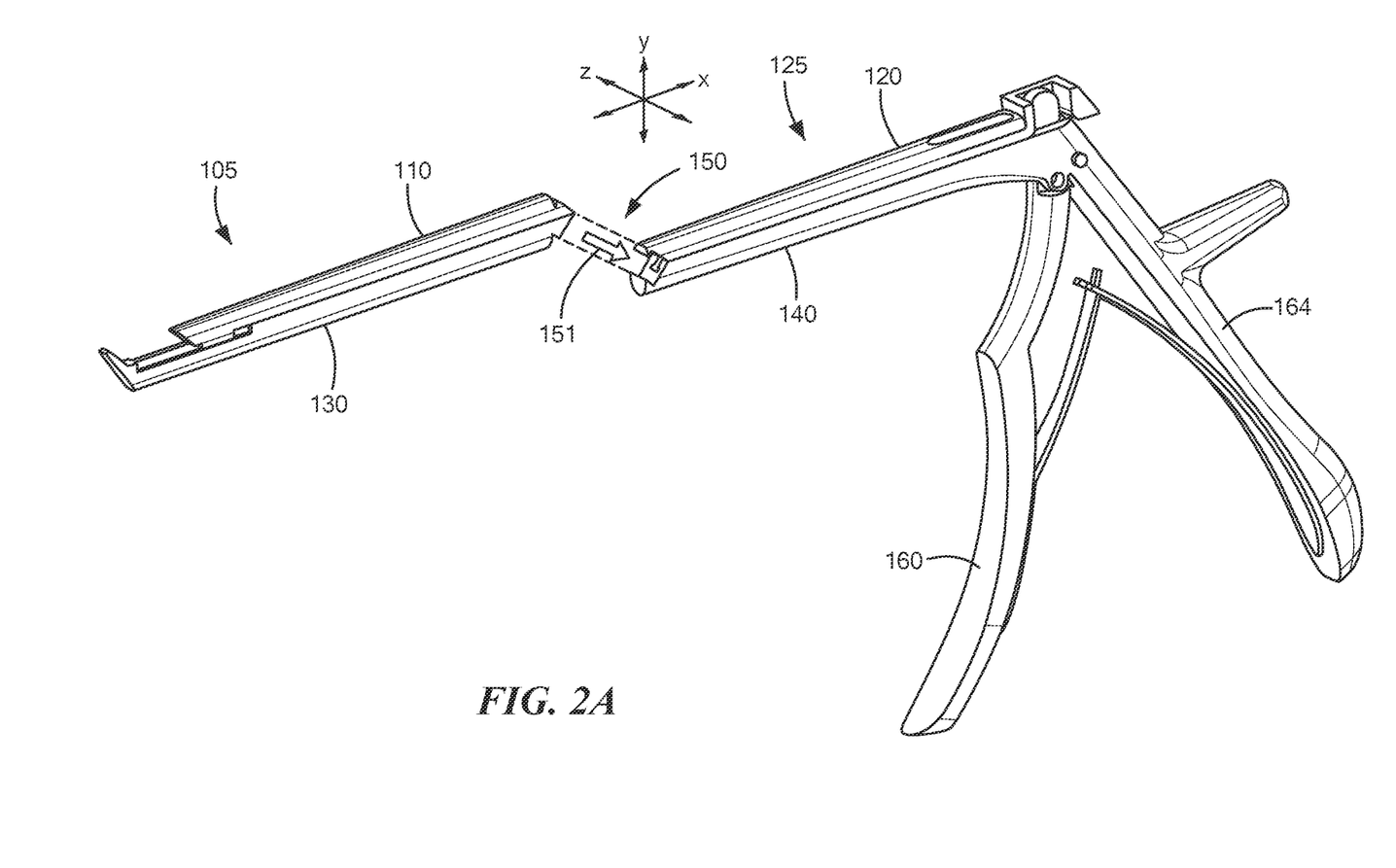
FIGS. 2A and 2B show detachment of a disposable shaft defining the tip of the rongeur device of FIGS. 1A-B.
Figure 2B:
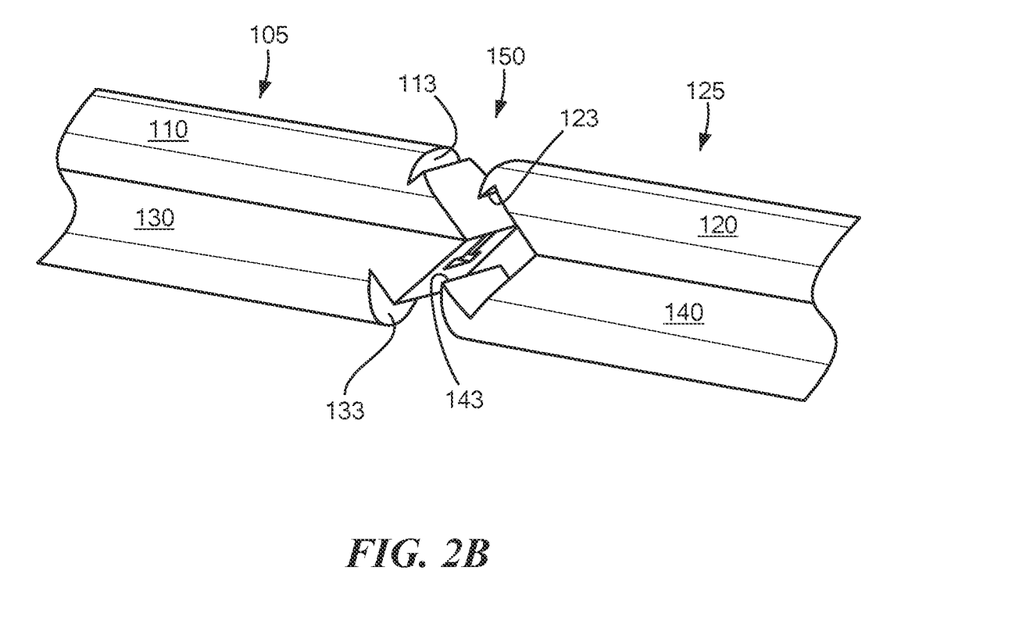

FIGS. 2A and 2B show detachment of a disposable shaft defining the tip of the rongeur device of FIGS. 1A-1B, Referring to FIGS. 1A-2B, the blade portion 110 and footplate portion 130 are slidable engaged at the rail 134 to form the tip 105. The interchangeable tip 105 may include a first tip 105 and a second tip, such that the detachable linkage 150 is adapted to engage the first tip 105 with the handle 125 at the detachable linkage 150, and perform a surgical procedure or access with the first tip 105. A successive procedure or excision may require a different tip or a fresh sterilized tip. In this instance, the first tip 105 is disengaged with the handle 125 via the detachable linkage 150, and an operator engages a second tip with the handle 125 via the detachable linkage. The detachable linkage 150 is configured to engage and disengage by movement in a lateral direction 151 to the longitudinal dimension of the device 100, such that slidably driven blade movement along the rail 134, 144 will not disrupt the linkage 150. The detachable linkage 150 is shown in more detail in FIG. 2B, including an upper cleat 123 opposing a lower cleat 143, which slide laterally into slots 113 and 133, respectively to engage the tip 105.

Figure 3A:
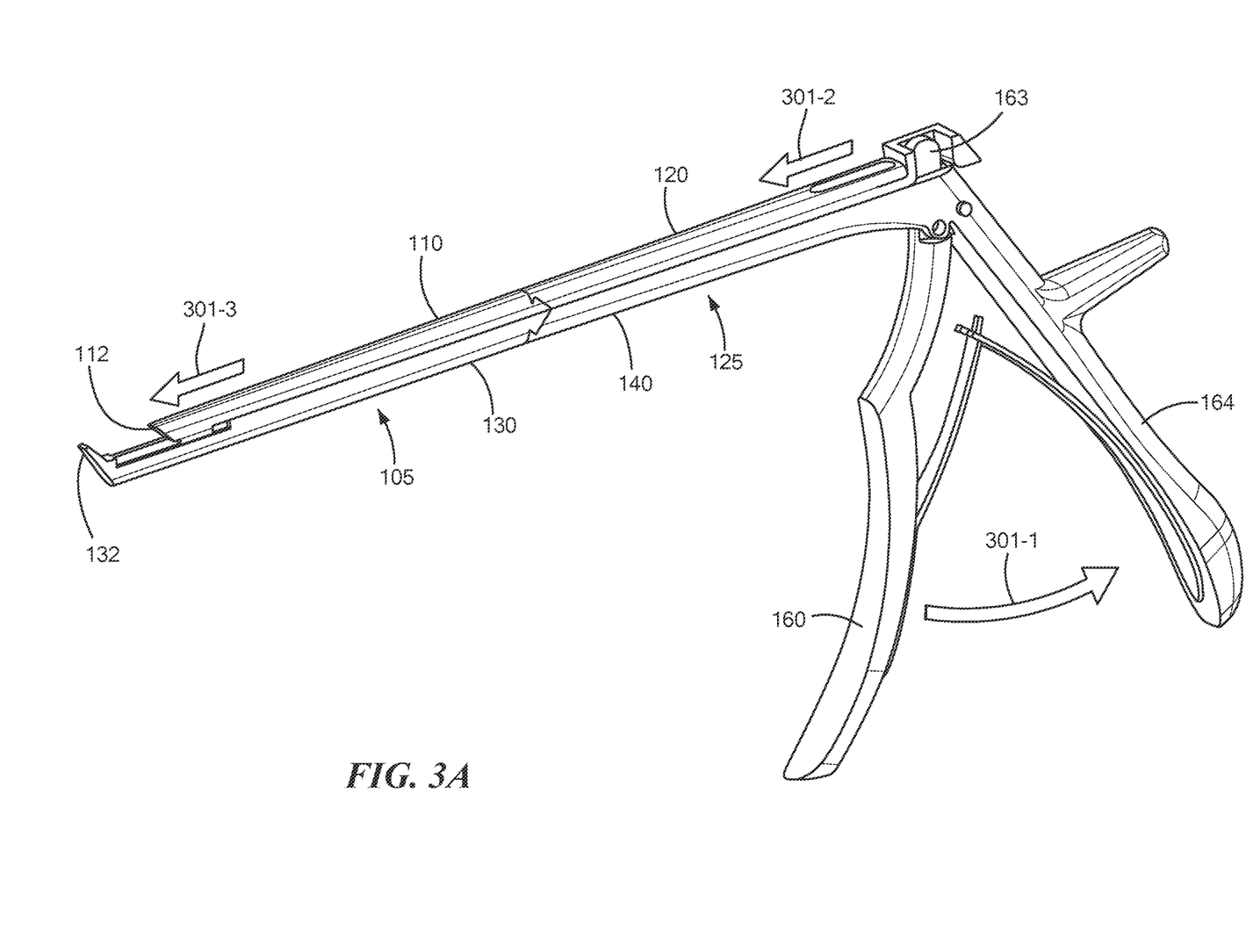
FIGS. 3A and 3B show attachment of the tip of the device in FIGS. 2A-B.
Figure 3B:
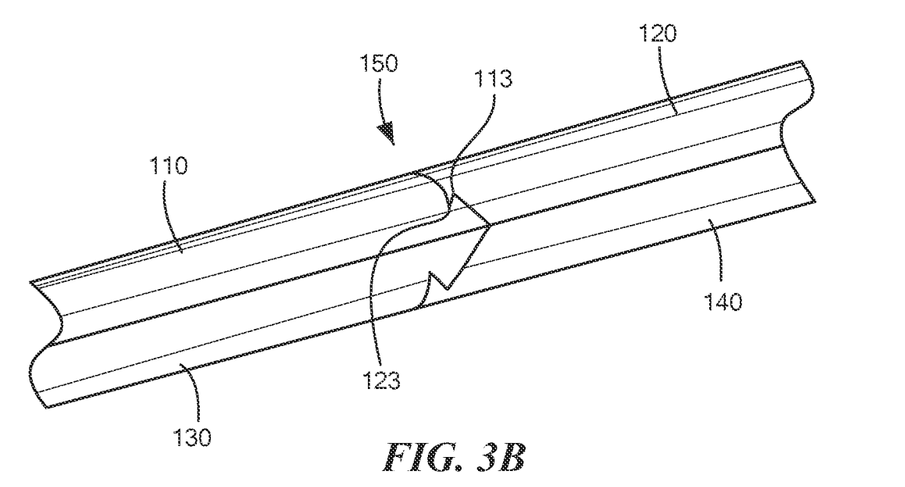

FIGS. 3A and 3B show attachment of the tip 105 of the device in FIGS. 2A-B. Referring to FIGS. 1A-3B, in the example configuration, the detachable linkage 150 forms an engagement that permits slidable communication of the handle slide 120 and blade portion 110 along the handle base 140 and footplate portion 130. The handle slide 120 and the blade portion 110 are aligned on the rail and in communication with the lever 160 for slidable actuation of the blade 112 against the footplate 132. With the linkage 150 engaged, handle 160 retraction toward the grip 164 (arrow 301-1) forces protrusion 163 forward against the handle slide 120, shown by arrow 301-2, and due to the engaged linkage, slides the blade portion 110 towards the footplate 132 (arrow 301-3) and closes the blade 112 against the footplate. FIG. 3B shows a closer view where retraction of the handle slide 120 pulls back the blade portion 110 from the upper cleat 123 engaged in the upper recession 113.

Figure 4A:
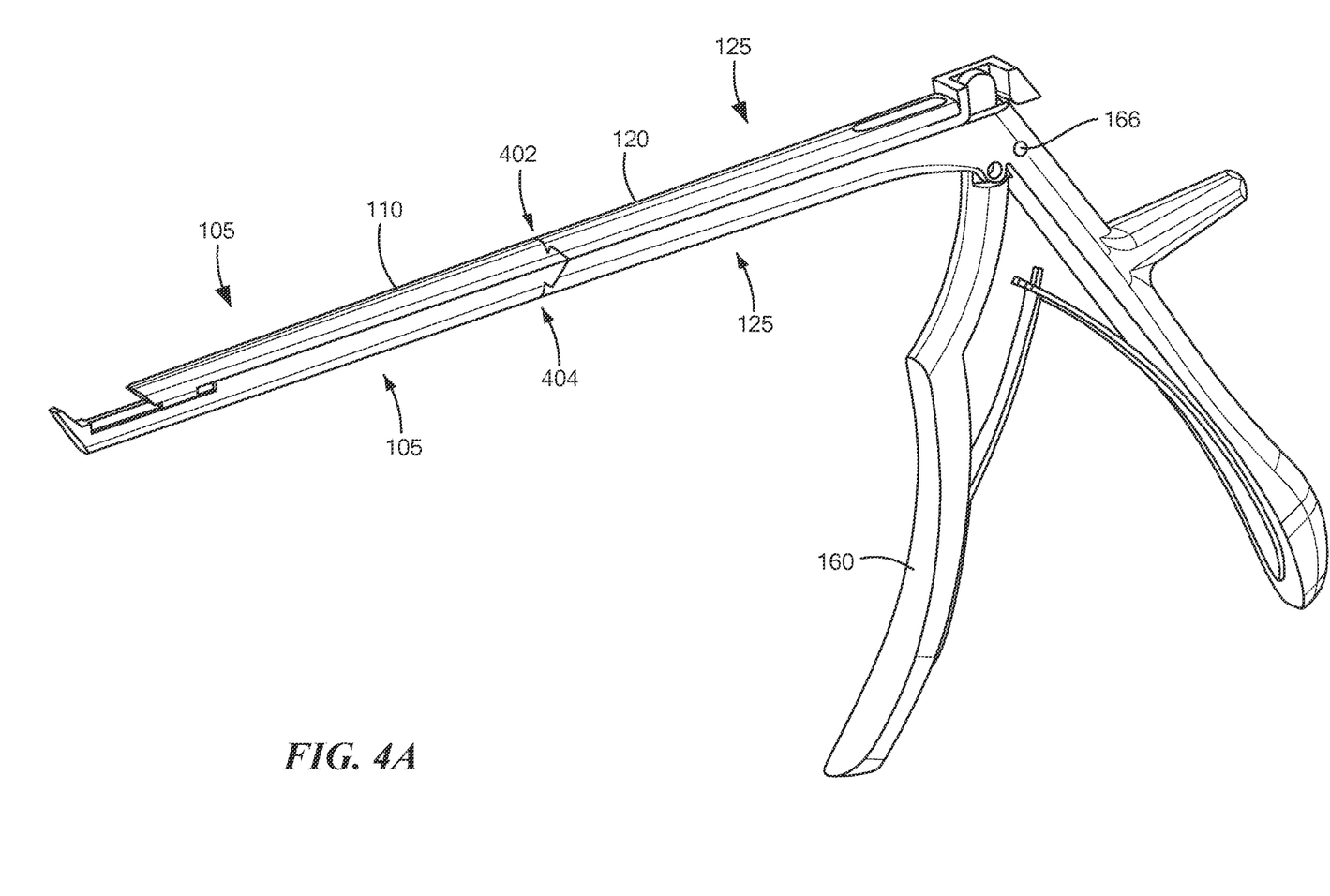
FIGS. 4A and 4B show locking the detachable linkage as in FIGS. 3A-B for usage.
Figure 4B:
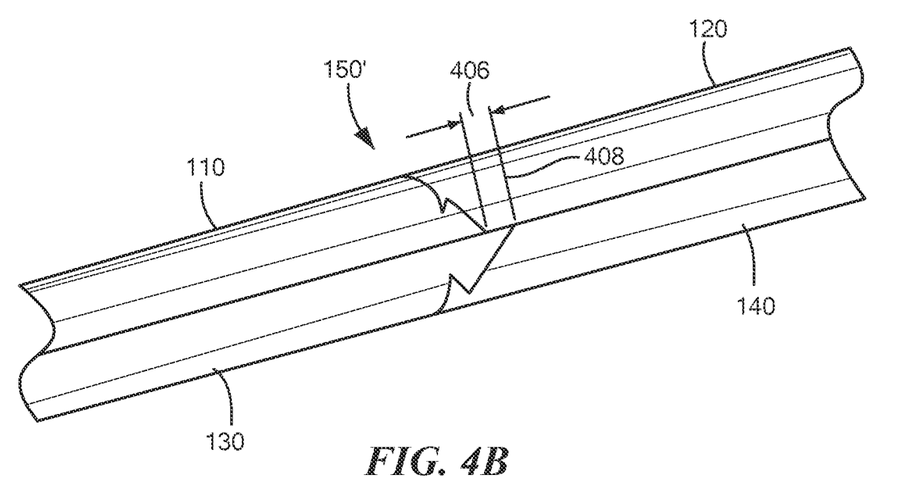

FIGS. 4A and 4B show locking the detachable linkage as in FIGS. 3A-3B for usage. From FIGS. 3A-4B, and looking more specifically at the detachable linkage 150, three positions are defined: engaged, locked, and actuated. FIGS. 3A and 3B show the tip 105 after lateral engagement with the handle 125. Following from FIG. 3A, in the engaged position, the handle 125 includes the handle base 140 and handle slide 120. The tip 105 includes the blade portion 110 and the footplate portion 130. The detachable linkage 150 joins the handle 125 and the tip 105 for engaging the blade portion 110 and the handle slide 120 in slidable communication with the footplate portion 130 and handle base 140.

Following a forward movement of the handle slide 120 and blade portion 110, an upper separation 402 of the detachable linkage is offset from a lower separation 404 between the footplate portion 130 and handle base 140. An interlocking member driven into an engaging slot by the advancing handle slide 120 locks the handle 125 and tip together, discussed further below. A locking position is achieved by a locking button 166 to permit the handle 160 to advance the handle slide 120 a distance 406 into a locked position 150' of the detachable linkage 150. This advancement does not dispose the blade 112 into the footplate 132; rather, further lever 160 movement advances the handle slide 120/blade portion 110 into the actuation range and against the footplate, while maintaining the handle 125 and tip locked. During the engagement, locked and actuation states, the blade portion 110 and handle slide 120 remain aligned longitudinally for actuation along a parallel axis with the footplate portion 130 and handle base 140 aligned longitudinally. In operation, lever 160 actuation by pulling towards a grip 164 causes the lever 160 to pivot around the pivot axis 162, which forces the protrusion 163 to force the handle slide 130 forward for engaging the blade, 112, discussed further below.

Figure 5A:
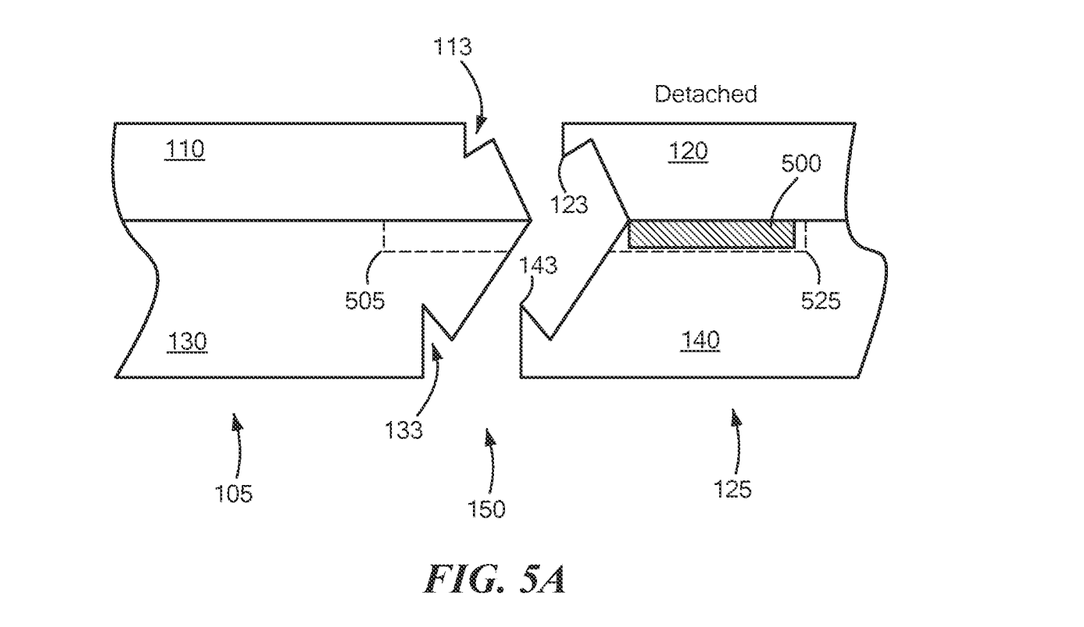
FIGS. 5A-5D show a cutaway view of the detachable linkage engaging, locking and disengaging the tip as in FIGS. 1A-4B.
Figure 5B:
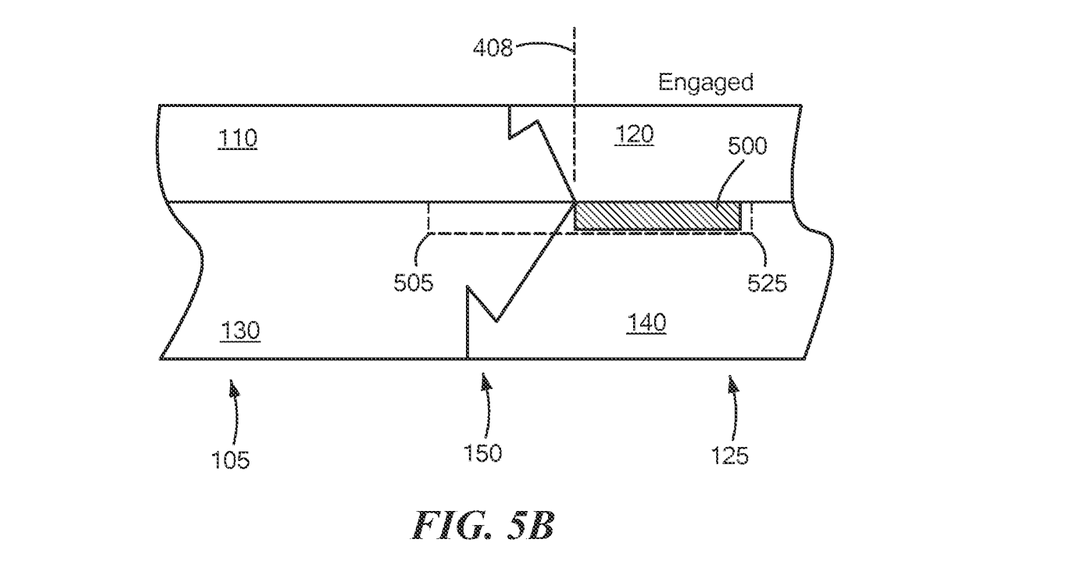

FIGS. 5A-5D show a cutaway view of the detachable linkage engaging, locking and disengaging the tip as in FIGS. 1A-4B. Referring to FIGS. 1A-5D, the sequence in FIGS. 5A-5D shows a progression through detached, engaged, locked, and actuated. These states follow when a new tip 105 is employed; the reverse applies to remove the tip 105 and install a new one. Reviewing the detachable linkage 150 and engaging features, the handle 125 includes the handle base 140 and handle slide 120. The tip 105 includes the blade portion 110 and the footplate portion 130. As the tip 105 approaches the handle 125 from the detached state in FIG. 5A, the detachable linkage 150 is defined by opposed cleats 123 (upper) and 143 (lower) on the handle slide 120 and handle base 140, respectively, adapted for engagement with corresponding receptacles 133 (lower) on the footplate portion 130 and 113 (upper) the blade portion 110, respectively. An interlocking member 500 on the handle base 125 resides in a slot 525, and is disposed in the slot up to a forward edge 408 of the slot for movement into an engaging slot 505 on the footplate portion 105. In FIG. 5B, the handle 125 is responsive to transverse movement of the tip 105 for engaging the detachable linkage 150.

As the tip 105 slides laterally (perpendicular to the longitudinal dimension of the tip 105 and handle 125) to engage the cleat 123 in the receptacle 113 and the cleat 143 in the receptacle 133, the detachable linkage 150 disposes the interlocking member 500 for longitudinal movement perpendicular to the transverse movement for engaging the engaging slot 505. The tip 105 is now engaged with the handle 125 but not locked.

Figure 5C:
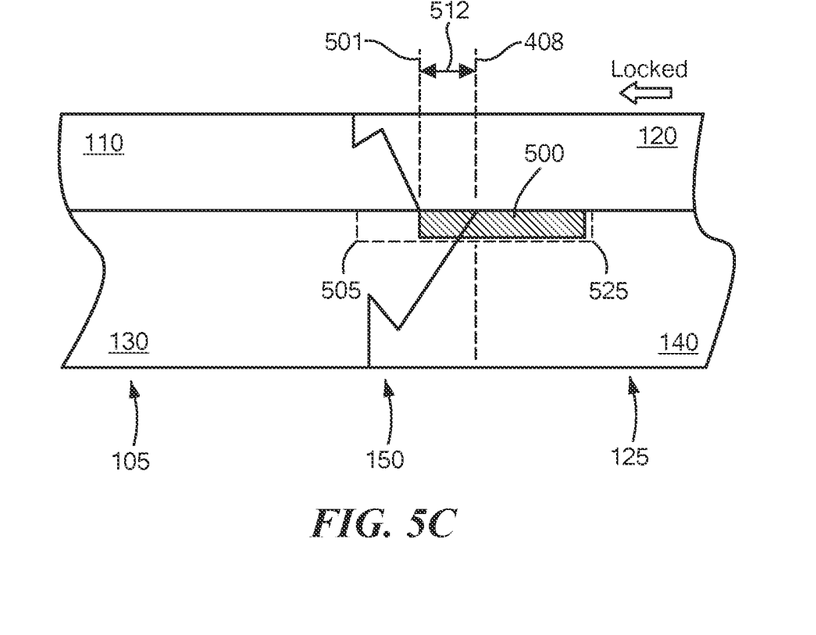

FIG. 5C shows the interlocking member 500 disposed in the engaging slot 505 for defining an interference fit against the transverse movement for locking the detachable linkage 150. As a leading edge 501 of the interlocking member 500 extends beyond the forward edge 408 of the handle 125, the engaged interlocking member defines an interference fit against the transverse, or lateral movement for locking the detachable linkage 150, by advancement of locking distance 512. The interlocking member 500 locks the tip 105 to the handle 125 by countering lateral movement (sideways) from sliding out of the cleats with an interference fit in the engaging slot 505. In combination with the cleats 123 and 143, the interlocking member prevents movement between the tip 105 and handle 125 with the exception of lever driven forward sliding of the handle slide 120 and blade portion 110 into the footplate 132.

Figure 5D:
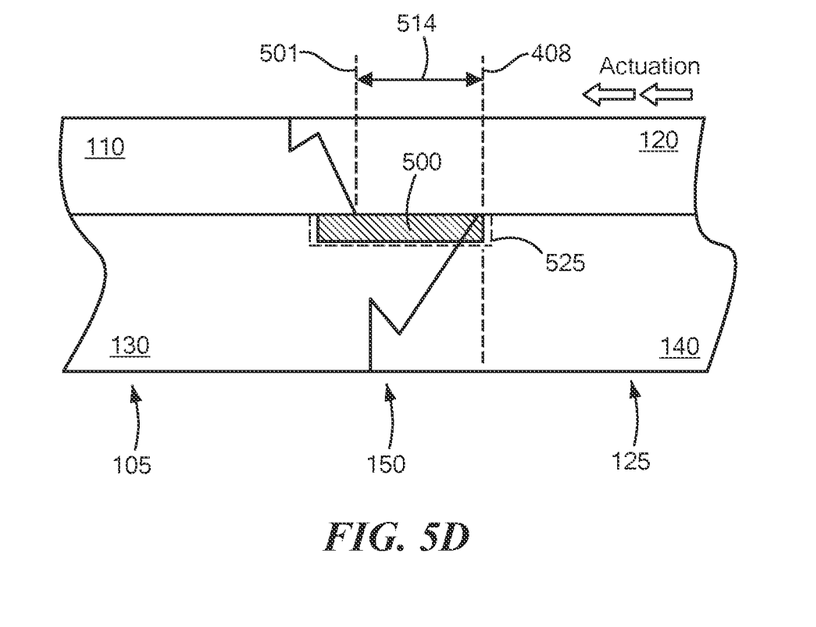

In FIG. 5D, actuated movement is shown by advancing the handle slide 120 further towards the footplate 132 for imparting cutting movement to the blade. Once the interlocking member 500 advances sufficiently to the locked position, further advancement maintains the locked position as the leading edge 501 of the interlocking member and the forward edge of the handle slide advance the blade portion 110 further forward relative to the footplate portion 130 for contacting the footplate 132 by the blade, shown by actuation distance 514.

Figure 6A:
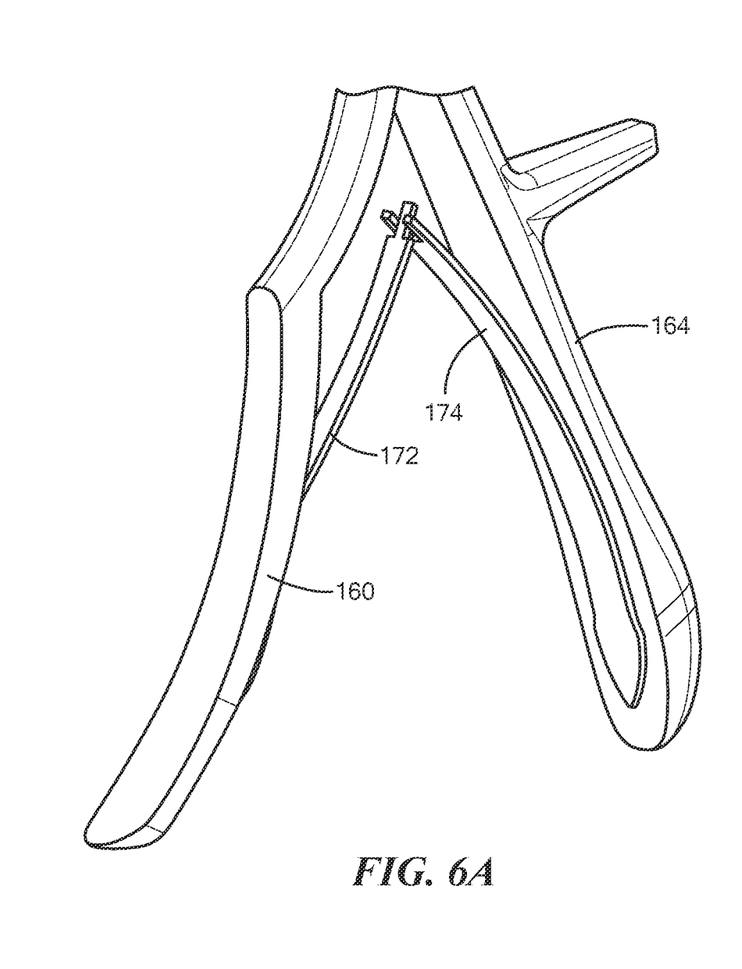
FIGS. 6A-6B show the handle and grip in the device of FIGS. 1A-5D.
Figure 6B:
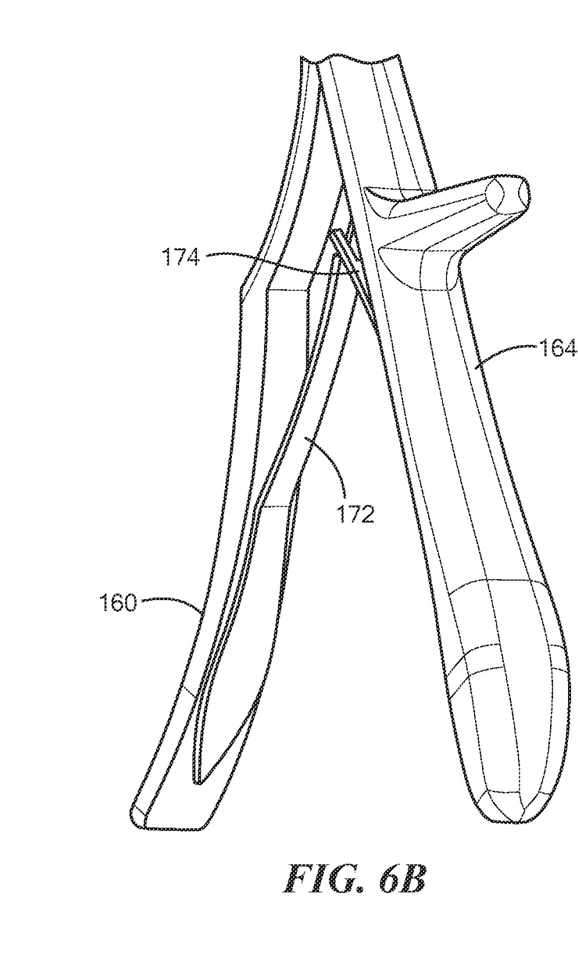

FIGS. 6A-6B show the handle and grip in the device of FIGS. 1A-5D. An amorphous metal structure imparts favorable strength and weight constructs to the device. Stainless steel has favorable characteristics in some conventional approaches, such as beneficial sterility properties. However, in a particular configuration, a Bulk Metallic Glass, which is metal in an amorphous glass phase, forms at least a portion of the device. It is beneficial in that, like plastic, it may be heated up to a certain degree temperature and injected it into specialty molds. This allows manufacturing of the device with little to no post processing. It also has better rigid mechanics characteristics than other surgical metals, such as stainless steel and titanium. The amorphous metal also has other favorable material properties for the disclosed surgical device. Being twice as strong as titanium, tougher and more elastic than ceramics, and having excellent wear and corrosion resistance makes them attractive for a variety of cutter/rongeur devices. In particular, an ability to mold and retain a sharp cutting edge is facilitated, as the blade may be directly formed without grinding and/or polishing as with conventional stainless steel or other workable metal.

Returning to FIG. 6, the handle 125 includes the handle base and handle slide, and the rail 144 attached to the handle base 140. The lever 160 attaches to the handle base at the pivot axis 162, such as an aperture, pin or hinge arrangement. The lever 160 advances in the direction of the grip 164 for locking and actuation of the linkage 150 as in FIGS. 5A-5D, as the grip 164 is an angled, rigid extension of the handle base 140. A forward leaf spring 172 and a rearward leaf spring 174 form a tabular hinge 176 from interlocked ends, and impose a spring bias to the lever 160. Locking button 166 allows the lever 160 to move from an engaged but unlocked position (FIG. 5B) to a locked position (FIG. 5C), and further to advance the blade portion 110 through the actuation range 514. Formation of the leaf springs 172, 174 from the amorphous metal material facilitates operation and sterilization.

Figure 7:
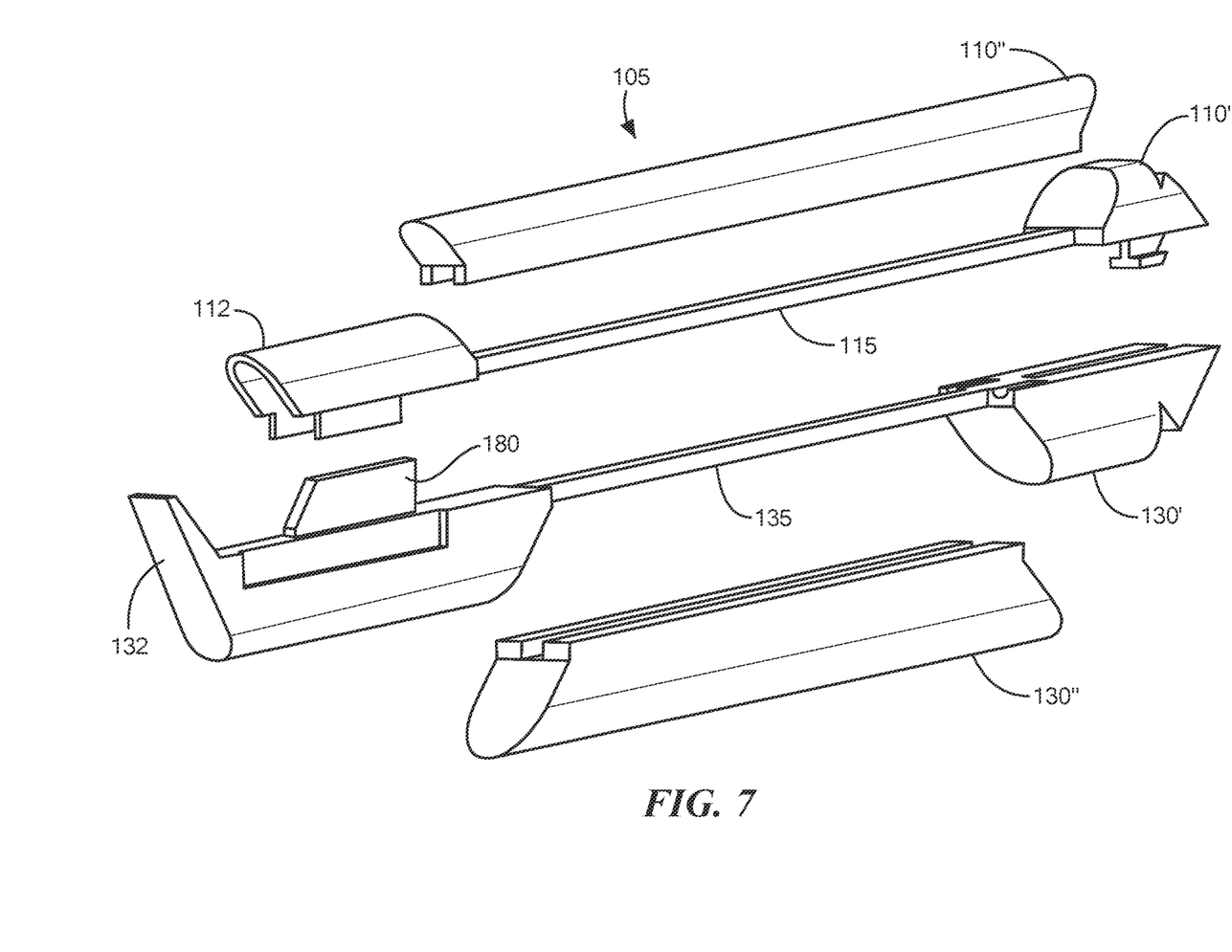
FIG. 7 shows amorphous metal construction in the tip in the device of FIGS. 1A-5D.

FIG. 7 shows amorphous metal construction in the tip in the device of FIGS. 1A-5D. A further use of amorphous metal such as bulk metallic glass applies in the formation of a series of tips 105 for varied cutting profiles, cutting edge renewal (replacement) and offline sterilization. Referring to FIGS. 1 and 7, the blade portion 110 and footplate portion 130 of the tip 105 include amorphous metal segments and polymer overlay segments. The blade portion 110 includes a metalglass segment 110', which includes the blade 112 and a narrow body 115 for continuity. As metalglass fabrication may be optimized by smaller, more specialized castings, an insert segment 110", formed from a polymer or similar easily molded material completes the blade portion 110. Similarly, the footplate portion 130 includes a metalglass segment 130', including the footplate 132 and an ejection tab 180 for forcing excised tissue upon blade retraction. An insert segment 130" complements the footplate portion 130, attached adjacent a narrow body 135 formed similar to narrow body 115.

Figure 8A:
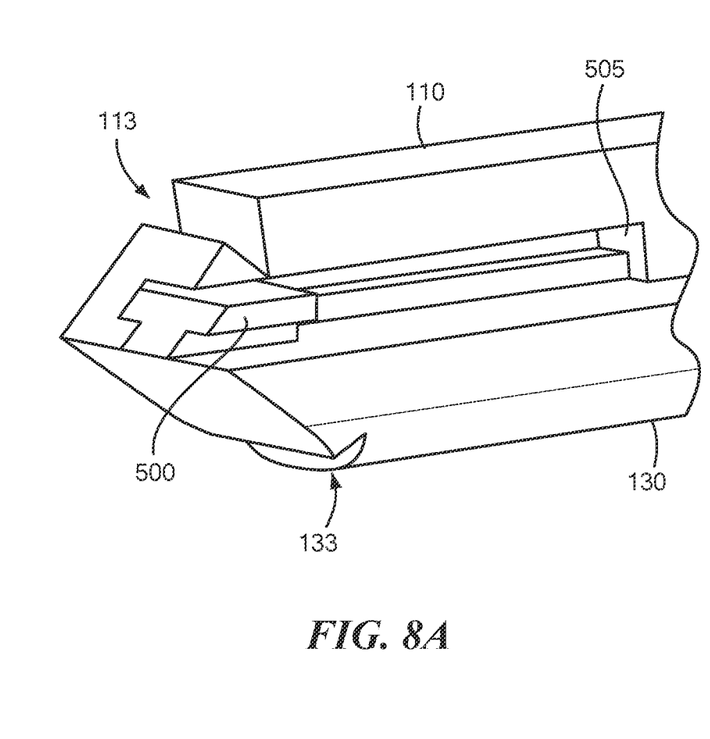
FIGS. 8A-8B show perspective end views of the detachable linkage on the handle as in FIGS. 1A-6B.
Figure 8B:
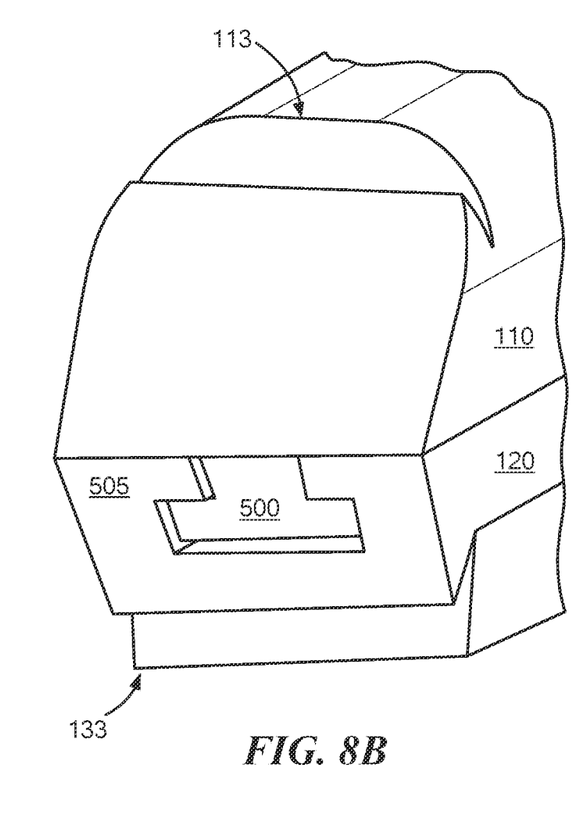

FIGS. 8A-8B show perspective end views of the detachable linkage 150 on the handle as in FIGS. 1A-6B. Referring to FIGS. 1, 5A-5D and 8A-8B the interlocking member 500 is defined by adjoined horizontal and vertical surfaces extending longitudinally along a length in a "T" shape, and the engaging slot 505 has a corresponding "T" profile. It can be further noted that one of the opposed cleats 113 may be disposed forward of the other of the opposed cleats 133 for offsetting the longitudinal alignment to increase stiffness.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A medical cutting device having interchanging blades, comprising:
    a blade disposed adjacent to a footplate for engaging with the footplate to sever surgical material;
    a lever pivoting about a pivot axis on a handle for disposing the blade against the footplate, the handle including a handle base and handle slide;
    an interlocking member on the handle base;
    an interchangeable tip including the blade, footplate and a rail, the blade in slidable communication with the rail for actuation against the footplate, the interchangeable tip including a blade portion and a footplate portion having an engaging slot; and
    a detachable linkage between the handle and the interchangeable tip for disengaging the interchangeable tip, the detachable linkage defined by opposed cleats on the handle base and handle slide adapted for engagement with corresponding receptacles on the footplate portion and the blade portion, respectively, and
    the handle responsive to transverse movement of the interchangeable tip for engaging the detachable linkage, the interlocking member disposed for longitudinal movement perpendicular to the transverse movement for engaging the engaging slot.

2. The device of claim 1 wherein the interchangeable tip includes a first tip and a second tip, the detachable linkage configured to:
    engage the first tip with the handle at the detachable linkage;
    disengage the first tip with the handle via the detachable linkage; and
    engage the second tip with the handle via the detachable linkage.

3. The device of claim 1 wherein the handle slide and the blade portion are aligned on the rail and in communication with the lever for slidable actuation of the blade against the footplate.

4. The device of claim 1, wherein
    the interlocking member is adapted for movement into an interference fit against the transverse movement for locking the detachable linkage.

5. The device of claim 4 wherein the interlocking member is disposed in the engaging slot for defining an interference fit against the transverse movement for locking the detachable linkage.

6. The device of claim 4 wherein the interlocking member is defined by adjoined horizontal and vertical surfaces extending longitudinally along a length in a "T" shape, and the engaging slot has a corresponding "T" profile.

7. The device of claim 1 wherein one of the opposed cleats is disposed forward of the other of the opposed cleats for offsetting the longitudinal alignment to increase stiffness.

8. The device of claim 1 wherein the blade portion and footplate portion include amorphous metal segments and polymer overlay segments.

9. The device of claim 1 wherein the blade has a cutting edge formed from amorphous metal.

10. A medical cutting device having interchanging blades, comprising:
    a blade disposed adjacent to a footplate for engaging with the footplate to sever surgical material;
    a lever pivoting about a pivot axis on a handle for disposing the blade against the footplate, the handle further including a handle base and handle slide;
    an interlocking member on the handle base;
    an interchangeable tip including the blade, footplate and a rail, the blade in slidable communication with the rail for actuation against the footplate; and
    a detachable linkage between the handle and the interchangeable tip for disengaging the interchangeable tip, the detachable linkage defined by opposed cleats on the handle base and handle slide adapted for engagement with corresponding receptacles on a footplate portion and a blade portion, respectively, wherein the interchangeable tip further includes the blade portion and the footplate portion having an engageable slot, the blade attached to a distal end of the blade portion and the footplate attached to a distal end of the footplate portion and aligned for communication with the blade,
    further comprising a rail on the handle, the rail on the handle aligned with the rail on the interchangeable tip when engaged by the detachable linkage, the blade portion responsive to the lever via aligned rail, the handle responsive to transverse movement of the interchangeable tip for engaging the detachable linkage, the interlocking member disposed for longitudinal movement perpendicular to the transverse movement for engaging the engaging slot.

11. The device of claim 10 wherein:
    the rail on the handle attached to the handle base,
    the lever attached to the handle base at the pivot axis; and
    the rail on the interchangeable tip attached to the footplate portion and aligned with the rail on the handle base, the handle slide and blade portion engaged by the detachable linkage for slidable communication along the rail.

12. A medical cutting device having interchanging blades, comprising:
    a blade disposed adjacent to a footplate for engaging with the footplate to sever surgical material;
    a lever pivoting about a pivot axis on a handle for disposing the blade against the footplate, the handle including a handle base and handle slide;
    an interlocking member on the handle base;
    an interchangeable tip including the blade, the footplate and a rail, the blade in slidable communication with the rail for actuation against the footplate, the interchangeable tip including a blade portion and a footplate portion having an engaging slot; and
    a detachable linkage between the handle and the interchangeable tip for disengaging the interchangeable tip, the detachable linkage joining the handle and the interchangeable tip for engaging the blade portion and the handle slide in slidable communication with the footplate portion and handle base, the detachable linkage defined by opposed cleats on the handle base and handle slide adapted for engagement with corresponding receptacles on the footplate portion and the blade portion, respectively;
    the blade portion and handle portion aligned longitudinally for actuation along a parallel axis with the footplate portion and handle base aligned longitudinally, and the handle responsive to transverse movement of the interchangeable tip for engaging the detachable linkage, the interlocking member disposed for longitudinal movement perpendicular to the transverse movement for engaging the engaging slot.

* * * * *